US005637456A

United States Patent [19]

Roth et al.

[11] Patent Number: 5,637,456
[45] Date of Patent: Jun. 10, 1997

[54] RAPID TEST FOR DETERMINING THE AMOUNT OF FUNCTIONALLY INACTIVE GENE IN A GENE THERAPY VECTOR PREPARATION

[75] Inventors: Jack A. Roth, Houston, Tex.; Wei Wei Zhang, Grayslake, Ill.; Bruno Tocque, Courbevoie; Laurent Bracco, Paris, both of France

[73] Assignees: The University of Texas, Board of Regents, Austin, Tex.; Rhone Poulenc Rorer, Antony Cedex, France

[21] Appl. No.: 390,887

[22] Filed: Feb. 17, 1995

[51] Int. Cl.[6] .................... C12Q 1/70; C12Q 1/68; C12N 7/01
[52] U.S. Cl. .................... 435/5; 435/6; 435/320.1
[58] Field of Search .................. 435/5, 6, 235.1, 435/240.2, 320.1; 935/32, 70, 71

[56] References Cited

U.S. PATENT DOCUMENTS

| 4,683,202 | 7/1987 | Mullis | 435/91.2 |
|---|---|---|---|
| 4,975,365 | 12/1990 | Grossman et al. | 435/6 |
| 5,212,057 | 5/1993 | Moyer et al. | 435/5 |

FOREIGN PATENT DOCUMENTS

| 92 03120 | 9/1993 | France . |
|---|---|---|
| WO93/03769 | 3/1993 | WIPO . |
| WO94/24297 | 10/1994 | WIPO . |
| WO95/02697 | 1/1995 | WIPO . |

OTHER PUBLICATIONS

International Search Report from PCT/US 96/02042, dated Jun. 26, 1996.
Abstract Book, 53rd Annual Meeting of The American Diabetes Association, Las Vegas Convention Center, Las Vegas, Nevada, Jun. 12–15, 1993.
Berkner, "Development of Adenovirus Vectors for the Expression of heterologous Genes," *BioTechniques*, 6(7):616–629, 1988.
Bett et al., "An efficient and flexible system for construction of adenovirus vectors with insertions or deletions in early regions 1 and 3," *Proc. Natl. Acad. Sci. USA*, 91:8802–8806, Sep., 1994.
Bishop, "The Molecular Genetics of Cancer," *Science*, 235:305–311, Jan., 1987.
Blau, "Muscling in on gene therapy," *Nature*, 364:673–675, Aug., 1993.
Bredenbeek et al., "Sindbis Virus Expression Vectors: Packaging of RNA Replicons by Using Defective Helper RNAs," *Journal of Virology*, 67(11):6439–6446, Nov., 1993.
Bridge et al., "Adenovirus Early Region 4 and Viral DNA Synthesis," *Virology*, 193:794–801, 1993.
Casey et al., "Growth suppression of human breast cancer cells by the introduction of a wild–type p53 gene," *Oncogene*, 6:1791–1797, 1991.
Challberg and Ketner, "Deletion Mutants of Adenovirus 2: Isolation and Initial Characterization of Virus Carrying Mutations Near the Right End of the Viral Genome," *Virology*, 114:196–209, 1981.

Cox et al., "Overexpression of dystrophin in transgenic mdx mice eliminates dystrophic symptons without toxicity," *Nature*, 364:725–729, Aug., 1993.
Deuring et al., "An unusual symmetric recombinant between adenovirus type 12 DNA and human cell DNA," *Proc. Natl. Acad. Sci. USA*, 78(5):3142–3146, May, 1981.
Fields and Jang, "Presence of a Potent Transcription Activating Sequence in the p53 Protein," *Science*, 249:1046–1049, Aug., 1990.
Friedmann, "Gene Therapy of Cancer through Restoration of Tumor–Suppressor Functions?," *Cancer* (Supplement), 70(6):1810–1817, Sep., 1992.
Friedmann, "Progress Toward Human Gene Therapy," *Science*, 244:1275–1281, Jun., 1989.
Fujiwara et al., "Induction of Chemosensitivity in Human Lung Cancer Cells in Vivo by Adenovirus–mediated Transfer of the Wild–Type p53 Gene," *Cancer Research*, 54:2287–2291, May, 1994.
Gluzman and Van Doren, "Palindromic Adenovirus Type 5–Simian Virus Hybrid," *Journal of Virology*, 45(1):91–103, Jan., 1983.
Ghosh–Choudhury et al., "Protein IX, a minor component of the human adenovirus capsid, is essential for the packaging of full length genomes," *The EMBO Journal*, 6(6):1733–1739, 1987.
Ghosh–Choudhury and Graham, "Stable Transfer of a Mouse Dihydrofolate Reductase Gene Into A Deficient Cell Line Using Human Adenovirus Vector," *Biochemical and Biophysical Research Communications*, 147(3):964–973, Sep., 1987.
Glorioso et al., "Herpes simplex virus–based vectors," *Virology*, 3:265–276, 1992.
Gómez–Foix et al., "Adenovirus–mediated Transfer of the Muscle Glycogen Phosphorylase Gene into Hepatocytes Confers Altered Regulation of Glycogen Metabolism," *The Journal of Biological Chemistry*, 267(35):25129–25134, Dec. 1992.
Graham and Prevec, "Adenovirus–Based Expression Vectors and Recombinant Vaccines," W. Doerfler (ed.), Adenovirus DNA, Martinus Nijhoff Publishing, Boston, pp. 363–390, 1986.
Grunhaus and Horwitz, "Adenoviruses as cloning vectors," *Virology*, 3:237–252, 1992.
Hearing and Shenk, "Functional Analysis of the Nucleotide Sequence Surrounding the Cap Site for Adenovirus Type 5 Region E1A Messenger RNAs," *J. Mol. Biol.*, 167:809–822, 1983.

(List continued on next page.)

*Primary Examiner*—David Guzo
*Assistant Examiner*—Robert Schwartzman
*Attorney, Agent, or Firm*—Arnold White & Durkee

[57] ABSTRACT

The present invention relates generally to the area of quality control for recombinant agents to be used in gene therapy. Specifically, the invention concerns an assay used to identify the percentage of defective or therapeutically inactive vector in a vector stock.

20 Claims, 2 Drawing Sheets

OTHER PUBLICATIONS

Hearing et al., "Identification of a Repeated Sequence Element Required for Efficient Encapsidation of the Adenovirus Type 5 Chromosome," *Journal of Virology*, 2555–2558, Aug., 1987.

Hermonat and Muzyczka, "Use of adeno–associated virus as a mammalian DNA cloning vector: Transduction of neomycin resistance into mammalian tissue culture cells," *Proc. Natl. Acad. Sci. USA*, 81:6466–6470, Oct., 1984.

Herz and Gerard, "Adenovirus–mediated transfer of low density lipoprotein receptor gene acutely accelerates cholesterol clearance in normal mice," *Proc. Natl. Acad. Sci. USA*, 90:2812–2816, Apr., 1993.

Hollstein et al., "p53 Mutations in Human Cancers," *Science*, 253:49–53, 1991.

Ishibashi et al., "Hypercholesterolemia in Low Density Lipoprotein Receptor Knockout Mice and its reversal by Adenovirus–mediated Gene Delivery," *J. Clin. Invest.*, 92:883–893, Aug., 1993.

Jaffe et al., "Adenovirus–mediated in vivo gene transfer and expression in normal rat liver," *Nature Genetics*, 1:372–378, Aug., 1992.

Ketner et al., "Complementation of adenovirus E4 mutants by transient expression of E4 cDNA and detection plasmids," *Nucleic Acids Research*, 17(8), 3037–3049, 1989.

La Salle et al., "An Adenovirus Vector for Gene Transfer into Neurons ad Glia in the Brain," *Science*, 259:988–990, Feb., 1993.

Lebkowski et al., "Adeno–Associated Virus: a Vector System for Efficient Introduction and Integration of DNA into a Variety of Mammalian Cell Types," *Molecular and Cellular Biology*, 8(10):3988–3996, Oct., 1988.

Lemarchand et al., "Adenovirus–mediated transfer of a recombinant human $\alpha_1$–antitrypsin cDNA to human endothelial cells," *Proc. Natl. Acad. Sci. USA*, 89:6482–6486, Jul., 1992.

Levine, "Tumor Suppressor Genes," *BioEssays*, 12(2)60–66, Feb., 1990.

Levrero et al., "Defective and nondefective adenovirus vectors for expressing foreign genes in vitro and in vivo," *Gene*, 101:195–202, 1991.

Majors, "Retroviral vectors–strategies and applications," *Virology*, 3:285–295, 1992.

Mastrangeli et al., "Diversity of Airway Epithelial Cell Targets for In Vivo Recombinant Adenovirus–mediated Gene Transfer," *The Journal of Clinical Investigation, Inc.*, 91:225–234, Jan., 1993.

McGrory et al., "Short Communications: A Simple Technique for the Rescue of Early Region I Mutations into Infectious Human Adenovirus Type 5," *Virology*, 163:614–617, 1988.

Miller, "Human gene therapy comes of age," *Nature*, 357:455–460, Jun., 1992.

Morgan et al., "Retroviral vectors containing putative internal ribosome entry sites: development of a polycistronic gene transfer system and applications to human gene therapy," *Nucleic Acids Research*, 20(6):1293–1299, 1992.

Mulligan, "The Basic Science of Gene Therapy," *Science*, 260:926–932, May, 1993.

Prevec et al., "Use of Human Adenovirus–based Vectors for Antigen Expression in Animals," *J. gen. Virol.*, 70:429–434, 1989.

Ragot et al., "Efficient adenovirus–mediated transfer of a human minidystrophin gene to skeletal muscle of mdx mice," *Nature*, 361:647–650, Feb., 1993.

Renan, "Cancer genes: current status, future prospects, and applications in radiotherapy/oncology," *Radiotherapy and Oncology*, 19:197–218, 1990.

Rich et al., "Development and Analysis of Recombinant Adenovirus for Gene Therapy of Cystic Fibrosis," *Human Gene Therapy*, 4:461–476, 1993.

Rosenfeld et al., "Adenovirus–Mediated Transfer of a Recombinant $\alpha$1–Antitrypsin Gene to the Lung Epithelium In Vivo," *Science*, 252:431–434, Apr., 1991.

Rosenfeld et al., "In Vivo Transfer of the Human Cystic Fibrosis Transmembrane Conductance Regulator Gene to the Airway Epithelium," *Cell*, 68:143–155, Jan., 1992.

Samulski et al., "Helper–Free Stocks of Recombinant Adeno–Associated Viruses: Normal Integration Does Not Require Viral Gene Expression," *Journal of Virology*, 63(9):3822–3828, Sep., 1989.

Spandidos and Anderson, "Oncogenes and Onco–Suppressor Genes: Their Involvement in Cancer," *Journal of Pathology*, 157:1–10, 1989.

Stratford–Perricaudet et al., "Evaluation of the Transfer and Expression in Mice of an Enzyme–Encoding Gene Using a Human Adenovirus Vector," *Human Gene Therapy*, 1L241–256, 1990.

Stratford–Perricaudet and Perricaudet, "Gene transfer into animals: the promise of adenovirus," *Human Gene Transfer*, Eds O. Cohen–Haguenauer, M. Boiron, Colloque INSERT/John Libert Eurotext Ltd., 219:51–61, 1991.

Stratford–Perricaudet et al., "Feasibility of adenovirus–mediated gene transfer in vivo," Bone Marrow Transplantation, Proceedings of the Symposium of Foetal and Neonatal Cell Transplantation and Retroviral Gene Therapy, 9(Suppl. 1):151–152, 1992.

Stratford–Perricuadet et al., "Widespread Long–term Gene Transfer to Mouse Skeletal Muscles and Heart," *J. Clin. Invest*, 90:626–630, Aug., 1992.

Su et al., "DNA looping between the origin of replication of Epstein–Barr virus and its enhancer site: Stabilization of an origin complex with Epstein–Barr nuclear antigen 1," *Proc. Natl. Acad. Sci. USA*, 88:10870–10874, Dec., 1991.

Travali et al., "Oncogenes on growth and development," *The FASEB Journal*, 4:3209–3214, Nov., 1990.

Walsh et al., "Regulated high level expression of a human $\gamma$–globulin gene introduced into erythroid cells by an adeno–associated virus vector," *Proc. Natl. Acad. Sci. USA*, 89:7257–7261, Aug., 1992.

Weinberg, "Tumor Suppressor Genes," *Science*, 254:1138–1146, Nov., 1991.

Willis and Menzel, "Adenovirus Vectors for Gene Therapy of Cancer," *Journal of Cellular Biochemistry*, Supplement 17E:204 Mar.–Apr., 1993.

Yonish–Rouach et al., "Wild–type p53 indices apoptosis of myeloid leukaemic cells that is inhibited by interleukin–6," *Nature*, 352:345–347, Jul., 1991.

Zhang et al., "Generation and Identification of Recombinant Adenovirus by Liposome–Mediated Transfection and PCR Analysis," *BioTechniques*, 15(5):868–872, 1993.

Zhang et al., "High–efficiency gene transfer and high–level expression of wild–type p53 in human lung cancer cells mediated by recombinant adenovirus," *Cancer Gene Therapy*, 1(1):5–13, 1994.

RAPID TEST FOR DETERMINING THE AMOUNT OF FUNCTIONALLY INACTIVE GENE IN A GENE THERAPY VECTOR PREPARATION

FIELD OF THE INVENTION

The present invention relates generally to the area of quality control for recombinant agents to be used in gene therapy. More specifically, the invention concerns an assay which can be used to assess the percentage of defective vector in a vector stock, where the vector encodes a therapeutic gene. Most specifically, the invention concerns a method for assessing the percentage of adenovirus containing a non-functional p53 gene in an adenovirus stock containing wild-type p53 to be used for clinical gene therapy.

DESCRIPTION OF RELATED ART

Current treatment methods for cancer, including radiation therapy, surgery and chemotherapy, are known to have limited effectiveness. For example, lung cancer alone kills more than 140,000 people annually in the United States. Recently, age-adjusted mortality from lung cancer has surpassed that from breast cancer in women. Although implementation of smoking-reduction programs has decreased the prevalence of smoking, lung cancer mortality rates will remain high well into the 21st century. The rational development of new therapies for lung cancer will depend on an understanding of the biology of lung cancer at the molecular level.

It is well established that a variety of cancers are caused, at least in part, by genetic abnormalities that result in either the over expression of one or more genes, or the expression of an abnormal or mutant gene or genes. For example, in many cases, the expression of oncogenes is known to result in the development of cancer. "Oncogenes" are genetically altered genes whose mutated expression product somehow disrupts normal cellular function or control (Spandidos et at., 1989).

Many oncogenes studied to date have been found to be "activated" as the result of a mutation, often a point mutation, in the coding region of a normal cellular gene, known as a "proto-oncogene." These mutations result in amino acid substitutions in the expressed protein product. This altered expression product exhibits an abnormal biological function that contributes to the neoplastic process (Travali et al., 1990). The underlying mutations can arise by various means, such as by chemical mutagenesis or ionizing radiation. A number of oncogenes and oncogene families, including ras, myc, neu, raf, erb, src, fms, jun and abl, have been identified and characterized to varying degrees (Travali et al., 1990; Bishop, 1987).

During normal cell growth, it is thought that some growth-promoting proto-oncogenes are counterbalanced by growth-constraining tumor suppressor genes. Several factors may contribute to an imbalance in these two forces, leading to the neoplastic state. One such factor is mutations in tumor suppressor genes (Weinberg, 1991).

One important tumor suppressor is the cellular protein, p53, which is a 53 kD nuclear phosphoprotein that controls cell proliferation. Point mutations in the p53 gene and allele loss on chromosome 17p, where the p53 gene is located, are among the most frequent alterations identified in human malignancies. The p53 protein is highly conserved through evolution and is expressed in most normal tissues. Wild-type p53 has been shown to be involved in control of the cell cycle (Mercer, 1992), transcriptional regulation (Fields et al., 1991), and induction of apoptosis (Yonish-Rouach et al., 1991, and, Shaw et al., 1992).

Various mutant p53 alleles are known in which a single base substitution results in the synthesis of proteins that have altered growth regulatory properties and, ultimately, lead to malignancies (Hollstein et al., 1991). In fact, the p53 gene has been found to be the most frequently mutated gene in common human cancers (Hollstein et al., 1991; Weinberg, 1991), and is particularly associated with those cancers linked to cigarette smoke (Hollstein et al., 1991; Zakut-Houri et al., 1985). The over-expression of mutated p53 in breast tumors has been documented (Casey et al., 1991).

One of the most interesting aspects of gene therapy for cancer relates to utilization of tumor suppressor genes, such as p53. It has been reported that transfection of wild-type p53 into certain types of breast and lung cancer cells can restore growth suppression control in cell lines (Casey et al., 1992). Although direct DNA transfection is not an efficient means for introducing DNA into patients' cells, these results serve to demonstrate that supplying tumor suppressors to cancer cells may be an effective treatment method if improved means for delivering tumor suppressor genes are developed.

Gene delivery systems applicable to gene therapy for tumor suppression and killing are currently being investigated and developed. Virus-based gene transfer vehicles are of particular interest because of the efficiency of viruses in infecting actual living cells, a process in which the viral genetic material itself is transferred to the target cell. Some progress has been made in this regard as, for example, in the generation of retroviral vectors engineered to deliver a variety of genes. Adenovirus vector systems have recently been proven successful in vitro and in animal studies in certain gene transfer protocols.

As the methods and compositions for gene therapy of cancer are improved, clinical treatments are becoming possible. This will require the large scale production of vector stocks. Such large scale production involves generating large amounts of sample vector stock from a "pioneer" vector stock arbitrarily designated as having 100% activity. Concerns arise over the loss of activity in this "scale-up." Clearly, quality control analysis of sample vector stocks will be a necessary step before any treatment regimen is undertaken. For example, it will be necessary to ensure that a sample vector stock contains sufficient active vector to mediate the intended therapeutic effect.

An important consideration expressed by the National Institutes of Health (NIH) Recombinant DNA Advisory Committee (RAC) and Federal Drug Administration (FDA) is the biological significance of these mutations in the final clinical stock. While it is highly unlikely that such mutant vectors would pose any risk to the patient or to those coming in contact with the patient, regulatory agencies will require a quality control analysis for clinical vector preparations. The NIH RAC has stated that the most important quality control aspect is biologic function. Thus, there is a need for an assay that evaluates the percentage of defective vectors in vector stocks for therapeutic use.

There remains, therefore, a clear need for the development of a quality control assay that evaluates the amount of defective or therapeutically inactive vector in a clinical vector stock and the concomitant loss of biologic activity in clinical vector stocks.

SUMMARY OF THE INVENTION

The present invention addresses the foregoing need by providing an assay for measuring the quality of vector preparations for therapeutic use. Specifically, a method for determining the percentage of defective or therapeutically inactive vectors in a sample vector stock is disclosed. It is envisioned that the method of the present invention can be utilized to quantitate loss of biological activity in a variety of therapeutic vector preparations.

In a general embodiment, the present invention provides a method of determining the percentage of defective vectors in a vector stock which is genetically engineered to contain an effector gene that inhibits tumor cell growth, induces tumor cell apoptosis or kills tumor cells. The method comprises the following steps:

a) contacting tumor cells with a vector stock under conditions permitting the introduction of vectors into tumor cells;

b) incubating tumor cells under conditions permitting growth of the cells;

c) assessing tumor cell growth after a sufficient period of time;

d) comparing the tumor cell growth with the growth of cells when contacted with one or more test standard stocks comprising positive control vectors carrying a functional effector gene and negative control vectors not carrying a functional effector gene.

Therefore, in a general sense, the first aspect of the present invention involves contacting tumor cells with a vector stock under conditions which allow importation into the tumor cells of the vector stock. The vector stock may be composed of a virion or plasmid that will infect the particular tumor cells of interest under conditions sufficient to permit such infection. The vector may contain various regulatory elements such as promoters and/or enhancers. The stock will contain from 0 to 100% functional effector gene. Specific examples of such vector stocks include but are not limited to viral vectors such as adenovirus, retrovirus, vaccinia virus, and adenoassociated virus. The tumor cell being contacted will be a target, subject to infection by, the particular vector stock employed for each particular assay. Examples of preferred tumor cells are lung, colon, breast, pancreas, prostate, head and neck, and skin cancer cells.

In a preferred embodiment, the present invention provides that vectors of the test standard stock lacking a functional effector gene, i.e., negative control vectors, encode a luciferase gene. An indicator gene is one that provides evidence of its successful incorporation into a vector. For instance, in a particularly preferred embodiment of the present invention, the indicator gene utilized is the luciferase gene which provides visual evidence of its incorporation. Conditions sufficient to allow infection of tumor cells with vector stock vary with the particular tumor cells and vectors employed in the assay. Such conditions are well known in the art.

Generally, the second aspect of the present invention involves incubating tumor cells under conditions permitting growth of the cells. Sufficient incubation time varies with the particular tumor cell and vector stock combination being assessed. A preferred period sufficient to allow tumor cell growth is between 2 and 10 days. In a preferred embodiment, utilizing an adenovims vector stock and SAOSLM tumor cells (American Type Culture Collection, Rockville, Md.), sufficient growth inhibition occurs in 3 to 5 days.

In a general sense, the third aspect of the present invention involves assessing tumor cell growth after a sufficient period of time. Growth can be assessed by cell counting techniques well known in the art.

Finally, the fourth aspect of the present invention generally involves comparing the growth of rumor cells infected with vector stock to standard test stocks comprising vectors containing known amounts of vector carrying a functional effector gene, i.e., positive control vectors, and negative control vectors. Functional effector gene refers to the therapeutic gene of interest which is theoretically contained in some amount in the vector stock being tested. Such effector genes include tumor suppressor genes, anti-sense constructs and toxins.

In a more preferred embodiment, the present invention provides that the vectors claimed are adenovirus vectors. Further, these adenovirus vectors can be contained within infectious adenovirus particles.

In yet another preferred embodiment, the therapeutic effector gene chosen to be incorporated into vector is a tumor suppressor. A particularly effective effector gene is the wild-type p53 gene.

In still another preferred embodiment, the percentage of statistically significant detectable defective vectors is between 0.5 and 10%. A most preferred embodiment dictates the percentage of statistically significant detectable defective vectors is greater than 0.5%.

Another embodiment of the present invention provides a kit comprising at least one receptacle which contains a test standard stock. The test standard stock or stocks included within the kit contain known percentages of defective vector compositions. In a preferred embodiment the defective vector composition or compositions are made up of vector incorporating the luciferase gene. In another preferred embodiment the kit may also have included a receptacle which contains a functional effector gene. In a preferred embodiment, the functional effector gene is the wild-type p53 tumor suppressor gene. In a most preferred embodiment, the kit includes receptacles of test standard stock mixtures containing vectors preparations encoding indicators genes in the percentages of 0%, 0.1%, 0.5%, 1.0%, 2.0%, 5.0%, 10%, 20% and 100%.

DETAILED DESCRIPTION OF THE PREFERRED EMBODIMENTS

Gene therapy is becoming a viable approach for the treatment of cancer. As the problems with target specificity, transfer and expression levels are solved, therapeutic gene constructs will become common tools for treating neoplastic disease.

Evaluation of vector stocks for use in gene therapy will be required for both safety and efficacy reasons. Molecular means for the analysis of vector stocks are not practical at this point in time; thus, reliance must be placed on biologic function. One way of standardizing biologic function is to produce test standard stocks of the therapeutic vector that mimic the biologic activity of vector stocks containing various percentages of defective vectors. It is potentially hazardous to create defective vectors containing mutated therapeutic genes to standardize evaluative assays. For example, a mutated p53 gene could be potentially harmful.

Therefore, an assay has been developed for determining the percentage of defective vector in a sample vector stock which utilizes a surrogate for defective vector.

According to the present invention, an assay is provided which measures diminution of wild-type function in a vector stock using defective vector. This defective vector represents a vector that has lost function during generation of the vector stock. In its most basic form, the defective vector is simply a vector without any inserted therapeutic gene but may also include an inactive or mutated therapeutic gene. The defective vector has no therapeutic effect on tumor cells because it expresses no therapeutic gene. In order to mimic the existence of defective vector, it is possible to mix a known defective vector, i.e., a negative control vector, with wild-type vector-effector stocks, i.e., positive control vectors. In a preferred example, such a negative control vector expresses an indicator gene like the luciferase gene (Adluc). Adluc serves as an indicator of the percentage of defective vector in the test stock.

VECTORS: The vectors that can be tested according to the disclosed assays may vary considerably. The vectors may be standard expression vectors that contain one or more effector genes and regulatory elements required for expression of the effector gene in cells. The regulatory elements will comprise at least a promoter and may also include structures that enhance the transcription of the effector gene (enhancers). The regulatory elements may include structures that permit expression of the effector in a limited class of cells (cell-specific promoters).

Where standard expression vectors are used, various methods for their introduction into cells will be employed. For example, the vectors may be encapsulated in liposomes, conjugated to targeting agents, attached to microparticles or otherwise modified to permit uptake or introduction into target cells. It also is contemplated that naked DNA may, in some instances, be sufficiently transported across cell membranes to be used in gene therapy. Whatever the transfer mechanism of choice or the form of the vector, an assay designed to test the activity of the vector stock will employ that mechanism.

Another form of vector is a viral vector. Viral vectors have been developed from a variety of different virus systems including adenovirus, herpesvirus, retrovirus, vaccinia virus and adeno-associated virus. These vectors have two advantages over standard expression vectors. First, the vectors can be engineered to replicate and encapsidate like infectious virus DNA. This permits the normal targeting and entry system of the virus to be usurped. In addition, the regulatory elements of the virus often are compatible with the gene expression machinery of the cells they infect. Of course, both host range and regulatory elements may be modified for a particular purpose.

EFFECTOR GENE: The effector gene encoded by the vector may be any gene that confers some detectable biologic activity on a tumor cell. Typically, the activity is growth inhibition, stimulation of programmed cell death (apoptosis) or direct cell killing. Various effector genes will have one or more these activities. For example, some tumor suppressor genes will inhibit the growth of tumor cells while others will restore normal programmed cell death of cells. p53 is a classic example of a tumor suppressor. Other tumor suppressors include RB, APC, DCC, NF-1, NF-2, WT-1, MEN-I, MEN-II, BRCA1, VHL, FCC and MCC. Oncogenes are appropriate targets for antisense constructs and include ras, myc, neu, raf, erb, src, fms, jun, trk, ret, gsp, hst, bcl and abl. Toxin genes or genes that block essential cells functions may inhibit the growth of minor cells or kill the cells outright. Toxins include cholera toxin, pertussis toxin, diphtheria toxin, tetanus toxin, ricin, endotoxin. Genes that render cells sensitive to an outside agent such as a cell surface antigen or thymidine kinase also will permit killing of cells.

CELLS: In theory, any tumor cell should be amenable to this sort of analysis. Of course, the tumor must be susceptible to the effector gene used. For toxins or genes that render cells susceptible to an outside agent, almost any cell will work. Antisense constructs and tumor suppressor will have to be tested with particular ramors to assess susceptibility. Lung, breast, colon, head & neck, pancreas, osteosarcoma and prostate tumor cells are exemplary of the cells that will be susceptible to treatment with the tumor suppressor p53.

ASSAY CONDITIONS: The conditions under which the assay is conducted will vary from assay to assay. For example, the condition under which treated cells are incubated and the time of incubation will vary depending on the particular assay. Where growth of cells is the assay read-out, the conditions and time period will vary according to the requirements of the cells involved. Where cell killing is the assay read-out, the conditions and time period will depend on the conditions and time necessary for the effector gene to kill cells. For other effector activities such as growth in soft agar or colony formation, the appropriate conditions, times and additional treatments will be clear to the skilled artisan.

SENSITIVITY: A sample vector stock will contain millions and sometimes trillions of vectors. An assay based on biological activity has a limited ability to identify defective vectors that exist at very low percentages. Depending on the particular kind of vector, the rumor cells being treated and the assay read-out, the threshold for statistically significant results will vary. Those of skill in the art can determine the sensitivity threshold of an assay simply by generating a series of test standard stocks.

For example, one will mix varying percentages of the negative control vector with a positive control vector (e.g., a sample of the pioneer vector stock) arbitrarily designated as having 100% activity. Of course, activity is defined relative to the vector-gene construct being tested. For instance, 100% activity of the positive control stock may be defined in terms of varying degrees of minor cell death, growth inhibition, apoptosis, or in terms of expression of an encoded gene. With some percentage of negative control vector added to the positive control stock, there will be statistically significant difference between the behavior (growth, killing, etc.) of cells treated with the positive control and the various positive-negative standard stock mixtures. This minimum statistically significant difference is the sensitivity level of the assay.

KITS: It will be desirable to provide kits for particular vector systems that contain, at a minimum, a negative control vector. Typically, these negative control vectors will encode a marker gene, like luciferase, that permits the user to monitor the amount of negative control vector that is in a test vector stock. Such kits also may contain trays or dishes suitable for culture of cells, dilution buffers and chambers, cells for propagation of the negative control vector, media and instructions.

ADENOVIRUS-p53: In a preferred embodiment, the assay is designed to measure the tumor suppression activity of an adenovirus-p53 construct (Adp53). While the mutation rate for viral vectors is not documented, the error rate for an adenovirus DNA polymerase is not expected to be higher than that for a mammalian DNA polymerase. Thus, it is possible that in a preparation of $10^{10}$ adenoviral particles there could be as many as $10^4$ copies of inactive or mutant p53 expressing adenoviruses.

The identification of mutant vectors by molecular means such as PCR is neither practical nor sufficient for this purpose. Moreover, since there is no assay for cell transformation mediated by mutant p53 by itself, it would be necessary to develop an assay to detect a cooperative event with another oncogene such as ras(2). Such assays are difficult to quantitate. Furthermore, many cells are not responsive to such a combination of genes. Also, this type of assay would also require as a positive control a mutant p53 vector. This has been prohibited by the RAC because of its potential hazard.

Specifically, the assay compares the activity of a pioneer stock of Adp53 vector with the activity of newly produced sample stocks. The pioneer stock of Adp53 is defined as mediating cell death in 100% of SAOS cells (human osteosarcoma cell line with a homozygous p53 deletion) at an MOI of 50:1 on the 5th day of culture. Such pioneer stocks eliminate tumors in vivo in an orthotopic model of human lung cancer growth in nude mice (Fujiwara et al., 1994; Zhang et at., 1993). By adding increasing amounts of defective vector to the pioneer stock (i.e., a stock of positive control vector), it is possible to mimic a sample stock with varying amounts of defective Adp53. The sample Adp53 is then tested for its ability to kill SAOS cells in 5 days and the growth curve compared to curves generated by test stocks with varying percentage of defective vector.

EXAMPLE

DETERMINATION OF THE PERCENTAGE OF DEFECTIVE VECTOR IN A SAMPLE LOT OF ADP53 ADENOVIRUS VECTOR STOCK

SAOS-LM cells (SAOS cell variant lung metastasis) were inoculated at $10^6$ cells per 60 mm culture dish. Dishes were then incubated at 37° C. overnight. The cells were counted prior to virus infection. Cells were infected at an MOI of 50:1. Groups included Adp53 pioneer, Adp53 stock containing 0.1%, .5%, 1%, 5%, 10%, and 20% Adluc (reconstituted positive controls), and the test lot of Adp53. All groups were set up in triplicate. Cells were counted daily (two counts per dish) for 5 days. The experiment was performed 3 times.

Figure 1:
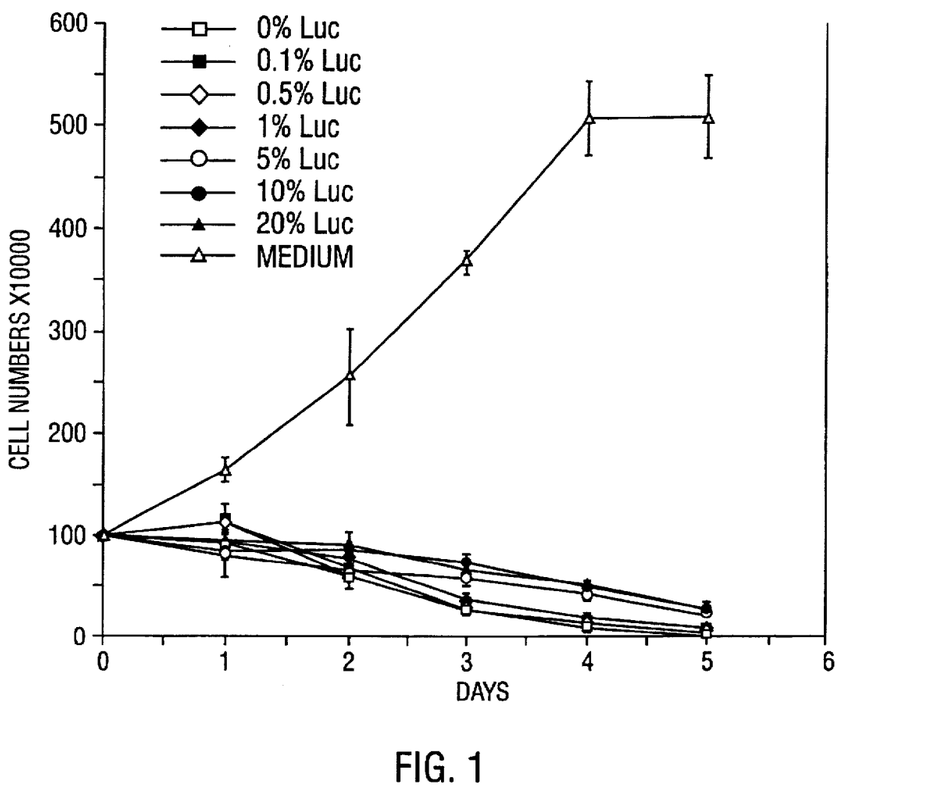
FIG. 1. Growth curves for SAOS-LM cells after incubation with medium, Adp53 and Adp53 containing varying amounts of Adluc. Each point represents the mean ISD for triplicate dishes.
Figure 2:
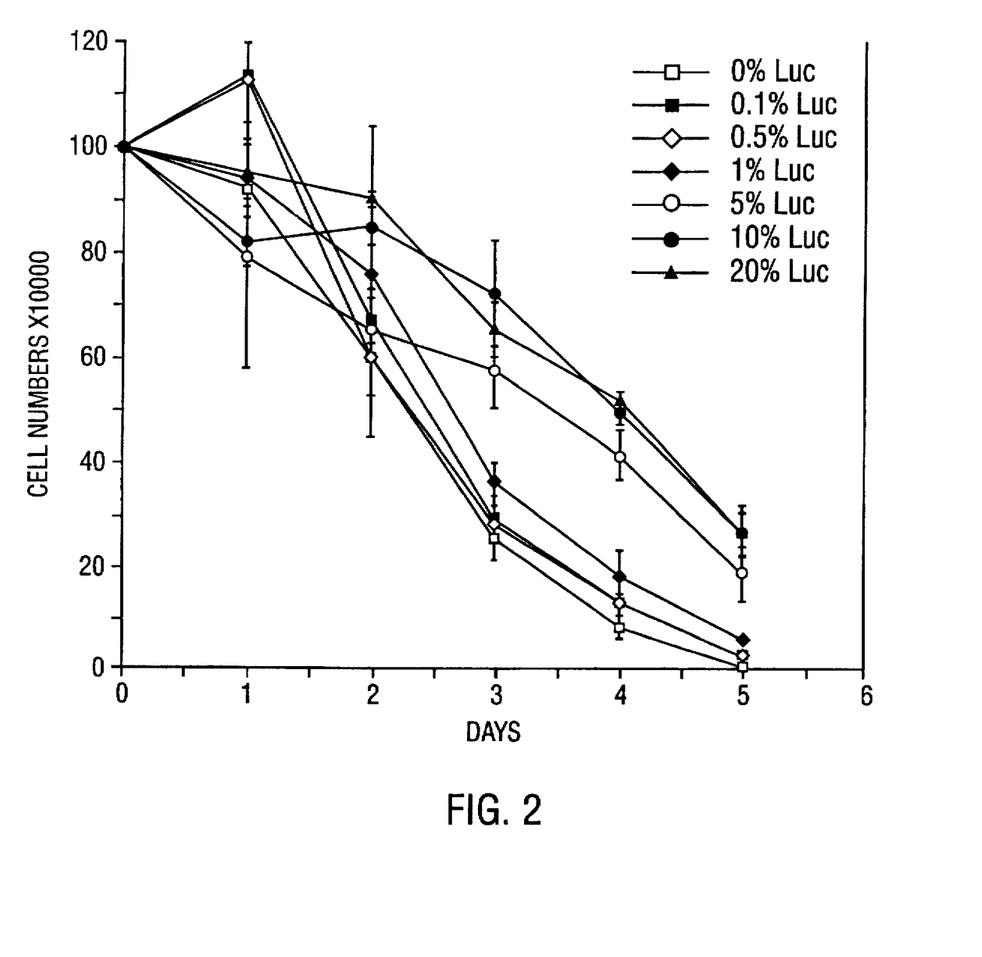
FIG. 2. Expansion of the growth curves from FIG. 1. Each point represents the mean ISD for triplicate dishes.

The results are shown in FIG. 1 and FIG. 2. FIG. 1 shows the profound inhibition of SAOS cells by Adp53 pioneer stock and the lesser inhibition where defective vector has been added. Statistically significant and reproducible differences can be measured by day 3 of the assay and is clearer at day 5. FIG. 2, for example, on day 3 the mean cell count was 25±4 (±S.D.) for Adp53 pioneer stock, and the mean cell count for Adp53 with 1% defective vector was 36±4. This difference is significant at the p<0.02 level. The limit of sensitivity for the assay appears to be 1% as the differences for 0.5% and 0.1% defective vector are not statistically significant. Thus the presence of 1% defective vector in a preparation is biologically significant and detectable reproducibly by this assay.

In conclusion, the development of a biologic standard combined with a surrogate for p53 mutant vector has resulted in the development of a sensitive bioassay for inactive vector. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The following references, to the extent that they provide exemplary procedural or other details supplementary to those set forth herein, are specifically incorporated herein by reference.

LITERATURE CITED

Bishop, Science, 235 305–311, 1985.

Casey, G., Lo-Hueh, M., Lopez, M. E., Vogelstein, B., and Startbridge, E. J., Growth suppression of human breast cancer cells by the introduction of a wild-type p53 gene. Oncogene 6: 1791–1797, 1991.

Fields et at., Science, 249: 1046–1049, 1990.

Fujiwara, T., Grimm, E. A., Mukhopadhyay, T., Zhang, W. W., Owen-Schaub, L., and Roth, J. A. Induction of chemosensitivity in human lung cancer cells in vivo by adenovirus-mediated transfer of the wild-type p53 gene. Cancer Res. 54: 2287–2291, 1994.

Hollstein, M., Sidransky, D., Vogelstein, B., and Harris, C., p53 mutations in human cancers. Science, 253: 49–53, 1991.

Mercer, W. E., Cell cycle regulation and the p53 rumor suppressor protein. Critic. Rev. Eukar. Gene Express, 2: 251–263, 1992.

Spandidos et al., J. Pathol. 157:1–10, 1989.

Travali et al., FASEB, 4:3209–3214, 1990.

Weinberg, R. A., Tumor suppressor gene. Science, 254: 1138–1145, 1991.

Yonish-Rouach et al., Nature, 352:345–347, 1991.

Zhang, W. W., Fang, X., Mazur, W., French, B. A., Georges, R. N., and Roth, J. A. High-efficiency gene transfer and high-level expression of wild-type p53 in human lung cancer cells mediated by recombinant adenovirus. Caner Gene Therapy, 1993. (in press)

What is claimed is:

1. A method for determining the percentage of inactive viral vectors in a sample vital vector stock, wherein at least some of the vectors in said stock carry an effector gone that encodes a product that inhibits growth of tumor cells, induces apoptosis of tumor cells or kills tumor cells, comprising the steps of:

a) introducing said sample vector stock into a culture of tumor cells;

b) introducing a negative control vector stock and at least one positive control vector stock into individual tumor cell cultures; and c) after a period of time, comparing the growth of the cell culture of step a) with the growth of the cell cultures of step b).

2. The method of claim 1, wherein said negative control vector stock encodes an indicator gene.

3. The method of claim 2, wherein said indicator gene is a luciferase gene.

4. The method of claim 1, wherein the vectors are selected from the group consisting of adenovirus, retrovirus, vaccinia virus and adeno-associated virus.

5. The method of claim 4, wherein said vectors are adenovirus vectors.

6. The method of claim 5, wherein said adenovirus vectors are contained within infectious adenovirus particles.

7. The method of claim 1, wherein said effector gene is a tumor suppressor gene.

8. The method of claim 1, wherein said effector gene induces apoptosis.

9. The method of claim 7, wherein said tumor suppressor gene is a wild-type p53 gene.

10. The method of claim 9, wherein said tumor cells are selected from the group consisting of lung, colon, breast, pancreas, prostate, head and neck and skin cancer cells.

11. The method of claim 1, wherein the limit of detection of said inactive vectors is greater than 0.05%.

12. The method of claim 1, wherein said period of time is between 2 to 10 days.

13. The method of claim 12, wherein said period of time is between 3 to 5 days.

14. The method of claim 1, wherein said control vector stocks comprise a percentage of inactive vectors of 0%, 0.1%, 0.5%, 1.0%, 2.0%, 5.0%, 10%, 20% or 100%.

15. A kit comprising at least one receptacle, wherein said receptacle includes a negative control vector stock, wherein at least some of the vectors in said stock carry an indicator gene.

16. The kit of claim 15, further comprising a second receptacle, said second receptacle including positive control vector stock.

17. The kit of claim 16, wherein said kit contains vector stocks comprising from 0% to 100% inactive vectors.

18. The kit of claim 17, wherein said control vector stocks comprise a percentage of vectors encoding said indicator gene of 0.1%, 0.5%, 10% 2 0% 5 0% 10% or 20%.

19. The kit of claim 15 wherein said indicator gene encodes luciferase.

20. The kit of claim 15, wherein said vectors are adenovirus vectors.

* * * * *

UNITED STATES PATENT AND TRADEMARK OFFICE
CERTIFICATE OF CORRECTION

PATENT NO.   :   5,637,456

DATED        :   June 10, 1997

INVENTOR(S)  :   Jack A. Roth, Wei Wei Zhang, Bruno Tocque and Laurent Bracco

It is certified that error appears in the above-identified patent and that said Letters Patent is hereby corrected as shown below:

In claim 1, column 8, line 45, delete the term "vital" and insert therefor the term --viral--.
In claim 1, column 8, line 46, delete the term "gone" and insert therefor the term --gene--.
In claim 7, column 9, line 4, delete the term "rumor" and insert therefor the term --tumor--.
In claim 18, column 10, line 12, delete the term "0.1%, 0.5%, 10% 2 0% 5 0% 10% or 20%" and insert therefor the term --0.1%, 0.5%, 1.0%, 2.0%, 5.0%, 10% or 20%--.

Signed and Sealed this

Second Day of September, 1997

*Attest:*

BRUCE LEHMAN

*Attesting Officer*   Commissioner of Patents and Trademarks

UNITED STATES PATENT AND TRADEMARK OFFICE
CERTIFICATE OF CORRECTION

PATENT NO. : 5,637,456
DATED : June 10, 1997
INVENTOR(S) : Jack A. Roth et al.

It is certified that error appears in the above-identified patent and that said Letters Patent is hereby corrected as shown below:

Column 9,
Lines 1 and 2, please delete "adenovims" and insert therefor -- adenovirus --.

Signed and Sealed this

Twenty-ninth Day of March, 2005

JON W. DUDAS
*Director of the United States Patent and Trademark Office*